(12) United States Patent
Cha et al.

(10) Patent No.: US 10,030,219 B2
(45) Date of Patent: Jul. 24, 2018

(54) NEUROVASCULAR UNIT(NVU)-ON-A-CHIP AND METHOD OF FABRICATING THE SAME

(71) Applicants: CHUNGBUK NATIONAL UNIVERSITY INDUSTRY-ACADEMIC COOPERATION FOUNDATION, Chungcheongbuk-do (KR); KOREA INSTITUTE OF SCIENCE AND TECHNOLOGY, Seoul (KR); Hong-Jun Lee, Gyeonggi-do (KR)

(72) Inventors: Sang-Hoon Cha, Chungcheongbuk-do (KR); Hong-Jun Lee, Gyeonggi-do (KR); Nakwon Choi, Seoul (KR); Hong-Nam Kim, Seoul (KR)

(73) Assignees: CHUNGBUK NATIONAL UNIVERSITY INDUSTRY-ACADEMIC COOPERATION FOUNDATION (KR); KOREA INSTITUTE OF SCIENCE AND TECHNOLOGY (KR); Hong-Jun Lee (KR)

( * ) Notice: Subject to any disclaimer, the term of this patent is extended or adjusted under 35 U.S.C. 154(b) by 24 days.

(21) Appl. No.: 15/011,385

(22) Filed: Jan. 29, 2016

(65) Prior Publication Data
US 2017/0211029 A1 Jul. 27, 2017

(30) Foreign Application Priority Data
Jan. 21, 2016 (KR) ........................ 10-2016-0007354

(51) Int. Cl.
| | |
|---|---|
| A61F 2/82 | (2013.01) |
| C12M 3/06 | (2006.01) |
| C12N 5/079 | (2010.01) |
| C12M 1/12 | (2006.01) |
| C12M 1/00 | (2006.01) |
| C12N 5/0793 | (2010.01) |
| C12N 5/0797 | (2010.01) |

(52) U.S. Cl.
CPC ............ *C12M 23/16* (2013.01); *C12M 25/14* (2013.01); *C12M 29/10* (2013.01); *C12N 5/0618* (2013.01); *C12N 5/0619* (2013.01); *C12N 5/0622* (2013.01); *C12N 5/0623* (2013.01); *C12N 2502/08* (2013.01); *C12N 2513/00* (2013.01); *C12N 2533/90* (2013.01)

(58) Field of Classification Search
CPC ........................................................ A61F 2/82
See application file for complete search history.

(56) References Cited

U.S. PATENT DOCUMENTS

| | | | | |
|---|---|---|---|---|
| 8,912,006 B2 * | 12/2014 | Achyuta | ................ | C12M 23/16 422/82.01 |
| 2014/0142370 A1 * | 5/2014 | Wong | ..................... | C12M 25/14 600/36 |

* cited by examiner

*Primary Examiner* — Ruth A Davis
(74) *Attorney, Agent, or Firm* — JHK Law; Joseph Hyosuk Kim

(57) ABSTRACT

Provided are a neurovascular unit (NVU)-on-a-chip and a method of fabricating the same, which 3-dimensionally integrates various human brain cells in a microfluidic platform by using a brain cell co-culture technique so as to simulate a similar environment to the human brain in vitro. The NVU-on-a-chip includes an extracellular matrix (ECM) simulation material (70) in a gel state; and at least one channel (75) which passes through the ECM simulation material (70) and perfuses a culture medium, in which the ECM simulation material (70) contains a plurality of types of human brain cells on an outer side of the channel (75), a brain microvessel endothelial cell lining (91) is formed on an inner side of the channel (75), and the plurality of types of human brain cells and the brain microvessel endothelial cell lining (91) contact each other through the channel (75) to simulate a blood brain barrier (BBB) of a human brain and a neurovascular unit (NVU) of the human brain including the BBB.

15 Claims, 6 Drawing Sheets

[FIG. 1]
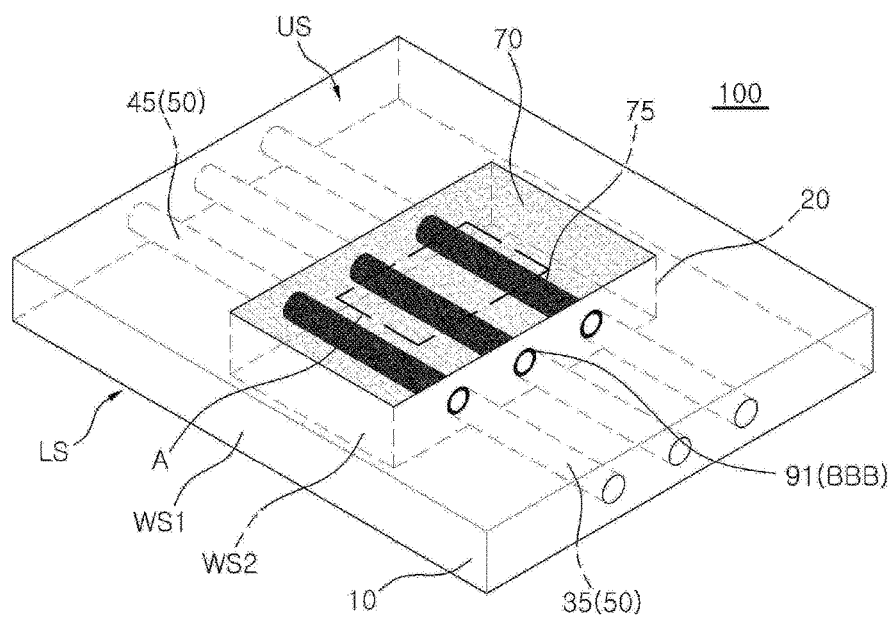
[FIG. 2]
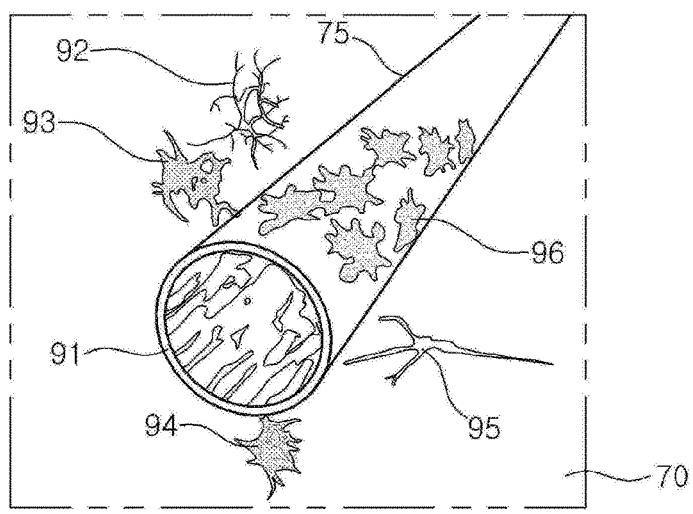

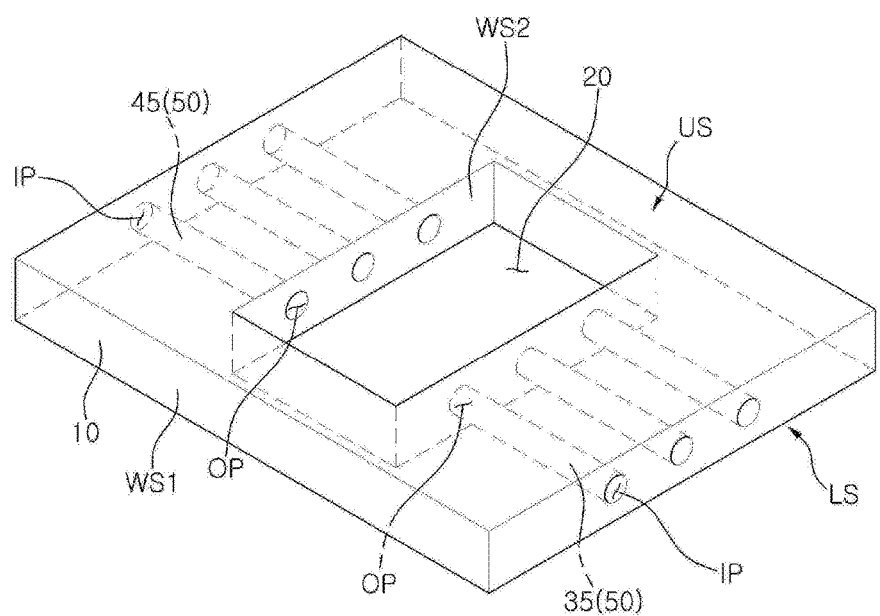

[FIG.4]
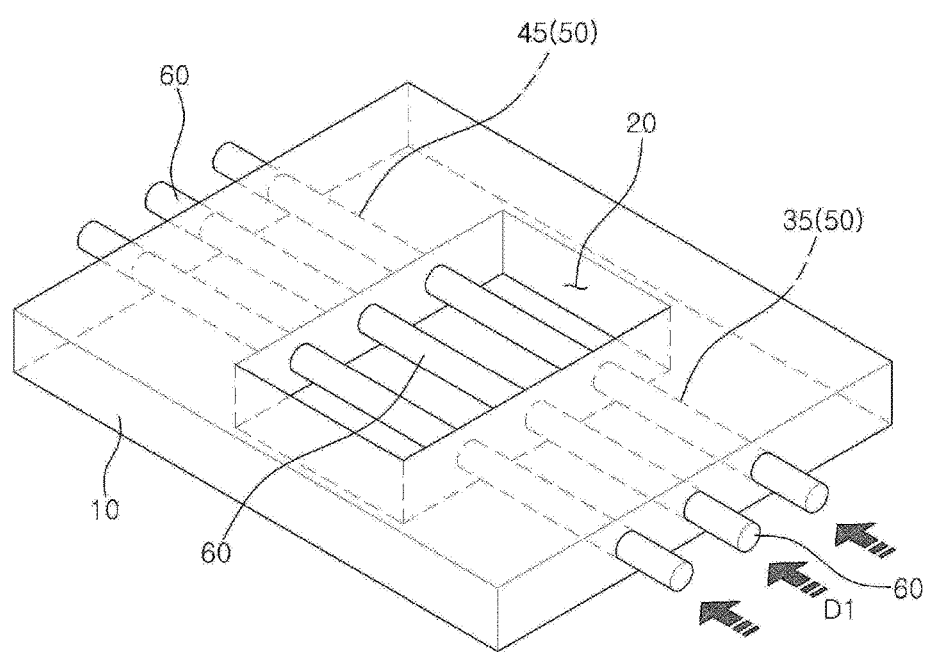

[FIG.5]
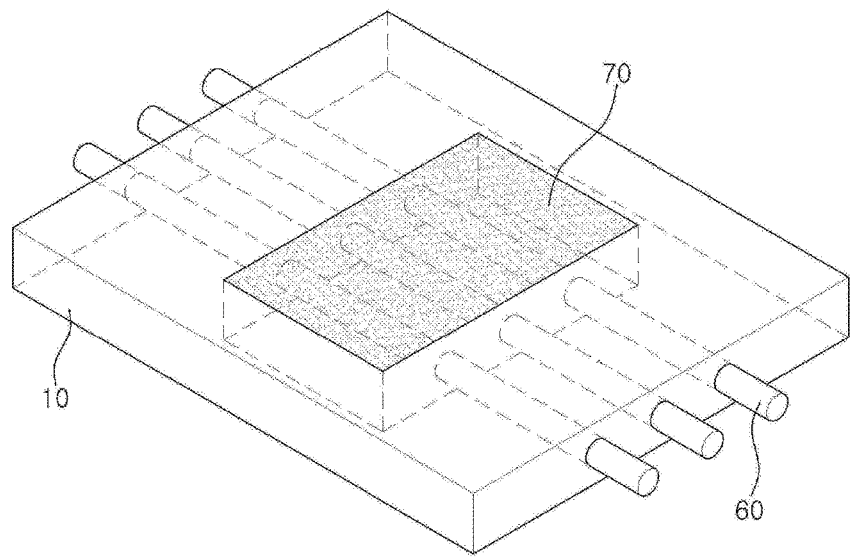
[FIG.6]
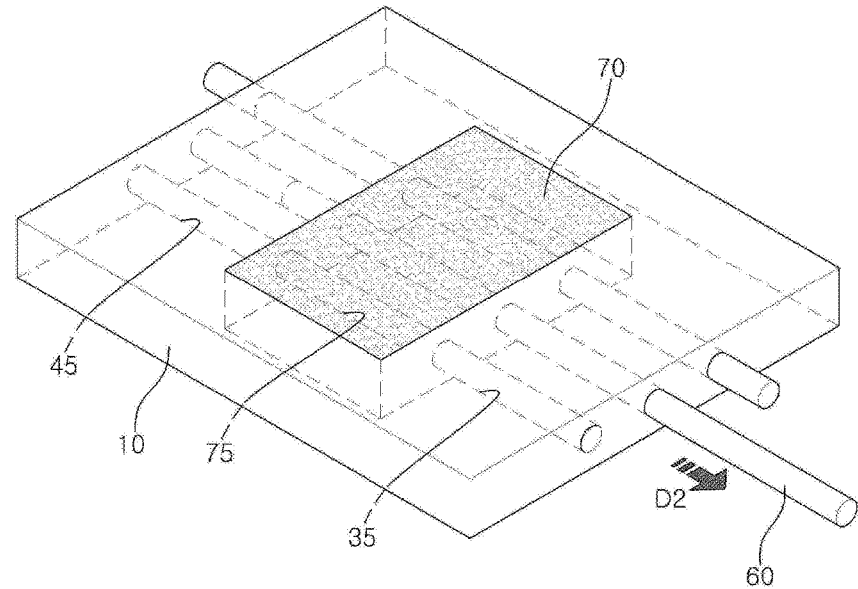

[FIG.7]
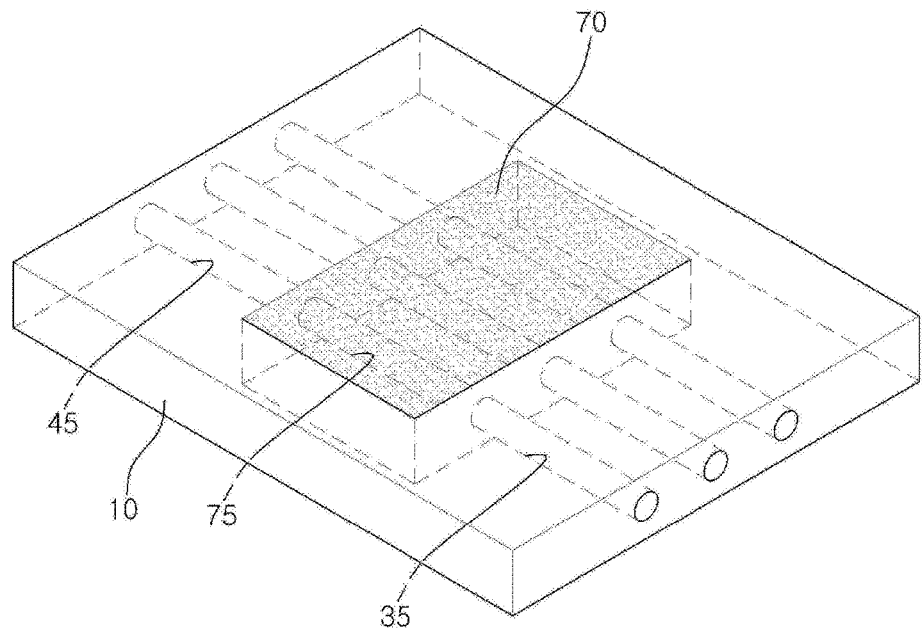
[FIG.8]
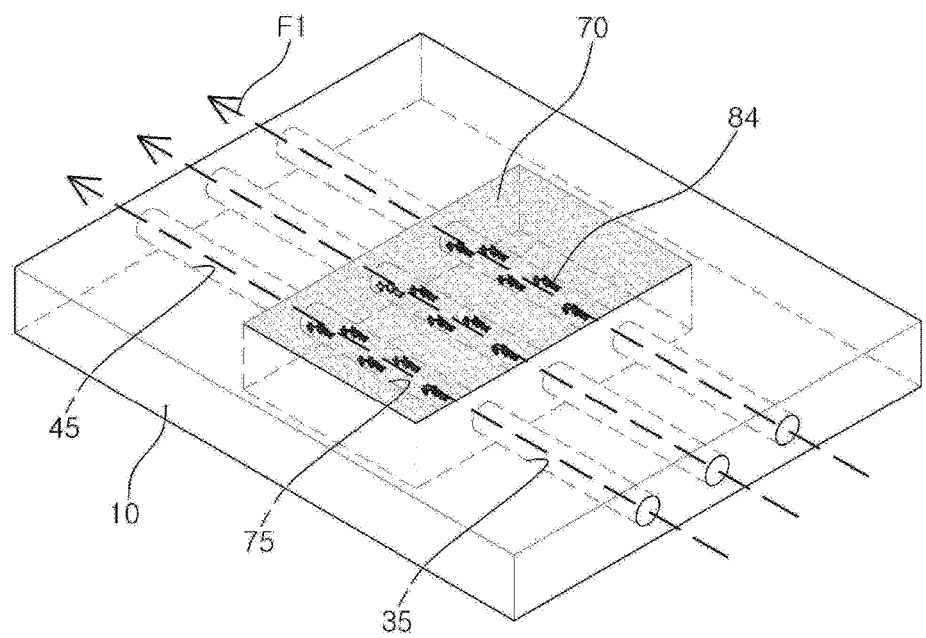

[FIG.9]
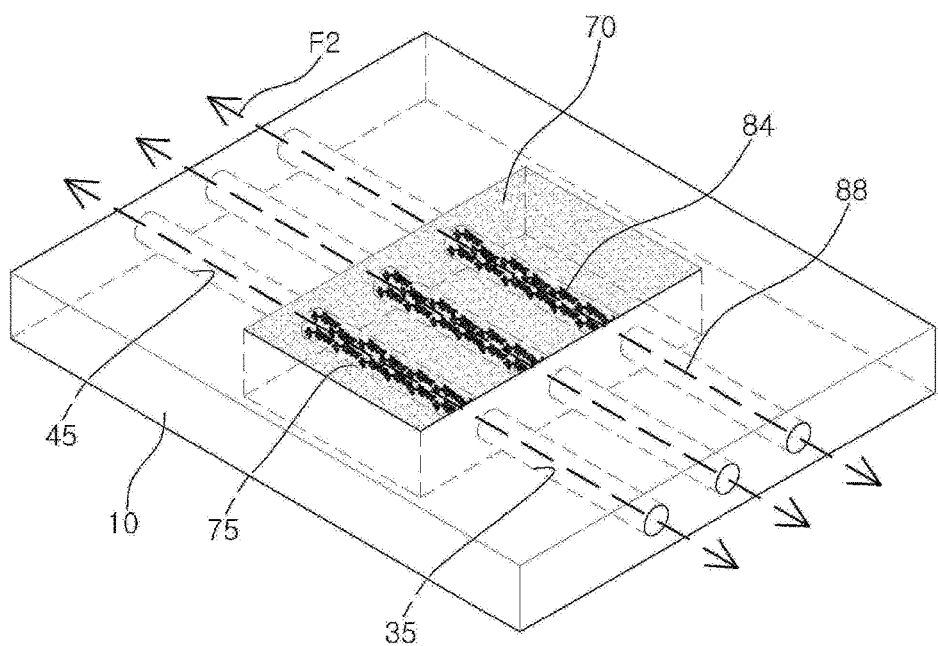

NEUROVASCULAR UNIT(NVU)-ON-A-CHIP AND METHOD OF FABRICATING THE SAME

CROSS-REFERENCE TO RELATED APPLICATIONS

This application is based on and claims priority from Korean Patent Application No. 10-2016-0007354, filed on Jan. 21, 2016, with the Korean Intellectual Property Office, the disclosure of which is incorporated herein in its entirety by reference.

TECHNICAL FIELD

The present disclosure relates to a microfluidic chip simulating the human brain in vitro and more particularly, to a neurovascular unit (NVU)-on-a-chip and a method of fabricating the same, which 3-dimensionally integrates various human brain cells in a microfluidic platform by using a brain cell co-culture technique so as to simulate a similar environment to the human brain including a blood-brain barrier structure in vitro for the new drug development and the personalized treatment related with brain diseases.

BACKGROUND

Although a two-dimensional (2D) cell culture model achieves recognition of the value in the biomedical science research, because the 2D cell culture model is performed using a petri dish to 2-dimensionally culture cells on a bottom of the petri dish, many cell types of tissue-specific and differentiated functions are not described or tissue functions and drug activity in vivo are not exactly predicted.

Particularly, in case of brain cells having a neuron and a neural stem cell which 3-dimensionally contact each other in vivo, owing to a limitation of the 2D cell culture model, an interest in a 3D cell culture model which simulates a spatial structure and biochemical complexity of living cells well has been increased.

The 3D cell culture model is performed, due to imitating a situation in vivo well, to implement a directional growth and complexity of cell-cell binding in an experiment in vitro. Further, the 3D cell culture model shows an improved cell survival and an enhanced neuronal differentiation as compared with the 2D cell culture model.

Accordingly, the 3D cell culture model is useful for identifying signaling pathways and drug responsiveness of various disease states well as compared with the 2D cell culture model in researching the molecular basis tissue function.

Meanwhile, for example, the 3D cell culture model was disclosed in an article (see the detailed description of the following 'related art') with a title of 'Recreating blood-brain barrier physiology and structure on chip: A novel neurovascular microfluidic bioreactor'.

The article proposed the 3D cell culture model which simulates a blood-brain barrier (BBB) by using a neurovascular microfluidic bioreactor in vitro. Herein, the BBB is composed of endothelial cells, pericytes, and astrocytes and functions as a gatekeeper limiting the transport of materials between a blood and a brain tissue.

That is, the BBB serves to send nutrients in the blood required to the brain tissue toward the brain from the blood and prohibit the entry of potentially harmful substances from a blood stream into the brain tissue. Herein, the neurovascular microfluidic bioreactor is configured to operate by using a first to a third polydimethylsiloxane (PDMS) layers which are sequentially laminated on a glass and a polycarbonate membrane between the first and second PDMS layers.

The membrane is a semi-permeable membrane and sets up a borderline between a microfluidic vasculature and brain compartments in the neurovascular microfluidic bioreactor. The first PDMS layer has two perfusion ports for vascular media supply in the endothelial cell and the second and third PDMS layers have four perfusion ports for brain media supply.

In order to grow cells at both sides of the membrane, first of all, the first PDMS layer is positioned at a higher level than the second and third PDMS layers and perfused through two perfusion ports in order to seed the endothelial cell in a conduit side of the membrane.

Next, after the first PDMS layer is positioned at a lower level than the second and third PDMS layers, the second and third PDMS layers are perfused through four perfusion ports in order to seed the neuron, the astrocyte, and the pericyte included in collagen in a brain side of the membrane.

Next, the endothelial cell, the neuron, the astrocyte, and the pericyte are cultured through a cell culture medium on the first and second PDMS layers to form the BBB around the membrane. However, the neurovascular microfluidic bioreactor is required to be reversed with respect to the first PDMS layer while forming the BBB, and a neurovascular unit (NVU) in vivo including the BBB, which are composed of the endothelial cell, the astrocyte and the pericyte, is not sufficiently implemented.

The reason is that the NVU has the endothelial cell positioned at the conduit side of the membrane and the astrocyte, the pericyte and the neuron positioned at the brain side of the membrane, which are separated by the membrane to be incompletely simulated from the viewpoint of a structure of the BBB in vivo, and also, other brain cells other than the endothelial cell, the pericyte, the neuron, and the astrocyte are further required from the viewpoint of the BBB in vivo and a structure therearound.

Further, the neurovascular microfluidic bioreactor 2-dimensionally cultures the endothelial cell along the membrane on the first PDMS layer to prevent the BBB in vivo from being sufficiently implemented and contacts the endothelial cell and the cell culture medium on the PDMS layer having a characteristic of absorbing air or drugs to show a different aspect from a mechanism in vivo related with the BBB.

Accordingly, because a simulation technique of the NVU in vitro which is developed in the related art shows the different aspect from the mechanism in vivo and has a problem in that efficacy of candidate drugs and predictability for the toxicity are low, for researches of the brain diseases, new drug development of the brain diseases, and patient-specific personalized treatment, development of an NVU on-a-chip having high degree of simulation is required.

RELATED ART

Non-Patent Document 17 persons other than Jacquelyn A. Brown, 'Recreating blood-brain barrier physiology and structure on chip: A novel neurovascular microfluidic bioreactor', BIOMICROFLUIDICS 9, 054124 (2015), pp. 054124-1 to 054124-15, (Received 24 Aug. 2015; accepted 10 Oct. 2015; published online 26 Oct. 2015)

SUMMARY

The present disclosure has been made in an effort to provide a neurovascular unit (NVU)-on-a-chip and a method of fabricating the same, which are suitable for maximally reproducing an NVU of the human brain in vitro by 3-dimensionally co-culturing five or more types of human brain cells in a single space which simulates an extra-cellular matrix (ECM) using a microfluidic platform technique of perfusing a culture medium.

An exemplary embodiment of the present disclosure provides a neurovascular unit (NVU)-on-a-chip including: an extracellular matrix (ECM) simulation material 70 in a gel state; and at least one channel 75 which passes through the ECM simulation material 70 and perfuses a culture medium, in which the ECM simulation material 70 contains a plurality of types of human brain cells on an outer side of the channel 75, a brain microvessel endothelial cell lining 91 is formed on an inner side of the channel 75, and the plurality of types of human brain cells and the brain microvessel endothelial cell lining 91 contact each other through the channel 75 to simulate a blood brain barrier (BBB) of a human brain and a neurovascular unit (NVU) of the human brain including the BBB.

The ECM simulation material 70 may include an extracelluar matrix including at least one of collagen, fibronectin, fibrin, fibrinogen, elastin, hyaluronic acid, proteoglycan, laminin, heparin sulfate, chondroitin sulfate, keratan sulfate and matrigel, hydrogel including at least one of alginate, polyethylene glycol, silicon hydrogel, polyacrylamide, polyethylene oxide, polypyrrolidone, glycosaminoglycan and polyhema, mixture of the extracellular matrix and the hydrogel, chemical variant of the extracelluar matrix, chemical variant of the hydrogel, or mixture of the chemical variant of the extracellular matrix and the chemical variant of the hydrogel.

The plurality of types of human brain cells may include one or more cells selected from the group consisting of a neuron 92, a neural stem cell 93, a microglia 94, an astrocyte 95, and a pericyte 96.

The plurality of types of human brain cells may include the neuron 92, the microglia 94, the astrocyte 95, and the pericyte 96.

The BBB may include the brain microvessel endothelial cell lining 91, the astrocyte 95, and the pericyte 96.

The NVU may include the BBB, the neuron 92, the neural stem cell 93, and the microglia 94.

The NVU-on-a-chip may further include a substrate 10 surrounding the ECM simulation material 70, in which the substrate 10 may be configured to mount the ECM simulation material 70 in a cell fixing well 20 which is positioned between a lower surface LS and an upper surface US so as to be extended toward the lower surface LS from the upper surface US passing through the upper surface US in a central region of the upper surface US.

The substrate 10 may include transparent ceramics including glass, silicon rubbers including at least one of polydimethylsiloxane (PDMS) and ecoflex, engineering plastics including at least one of polystyrene, polymethylmethacrylate, polypropylene, polycarbonate and polyurethane, mixture including at least two of the transparent ceramics, the silicon rubbers and the engineering plastics, chemical variant of the transparent ceramics, chemical variant of the silicon rubbers, chemical variant of the engineering plastics, or mixture including at least two of the chemical variant of the transparent ceramics, the chemical variant of the silicon rubbers and the chemical variant of the engineering plastics.

The substrate 10 may include a passage 50 having the same number as the channel 75, and the passage 50 may be divided into a first passage 35 and a second passage 45 at both sides of the cell fixing well 20 to pass through the substrate 10 and fluidly communicate with the channel 75.

The substrate 10 and the cell fixing well 20 may be quadrangular in shape and have a first side wall WS1 and a second side wall WS2, respectively, the first side wall WS1 may have a larger height than the second side wall WS2 in a thickness direction of the substrate 10, the first side wall WS1 and the second side wall WS2 may come into contact with the upper surface US while forming an angle with the upper surface US to face each other, and each of the first passage 35 and the second passage 45 may be opened in the first side wall WS1 of the substrate 10 and the second side wall WS2 of the cell fixing well 20 facing the first side wall WS1 to have an inlet port IP and an outlet port OP located respectively in the first side wall WS1 and the second side wall WS2.

The 3D co-culture in which the NVU of the human brain including the BBB is simulated may be performed by bringing the outer side of the channel 75 into contact with the ECM simulation material 70, and a tested drug may be negligibly absorbed on the substrate 10 by minimizing the contact between the substrate 10 and the channel 75 to avoid showing a different aspect from a mechanism in vivo.

Another exemplary embodiment of the present disclosure provides a method of fabricating a neurovascular unit (NVU)-on-a-chip including: forming a channel 75 passing through an extracellular matrix (ECM) simulation material 70 containing a plurality of types of human brain cells in a gel state; forming a brain microvessel endothelial cell lining 91 on an inner side of the channel 75; and simulating a blood brain barrier (BBB) of a human brain and a neurovascular unit (NVU) of the human brain including the BBB through the channel 75 by using the brain microvessel endothelial cell lining 91 and the plurality of types of human brain cells.

The ECM simulation material 70 may include an extracelluar matrix including at least one of collagen, fibronectin, fibrin, fibrinogen, elastin, hyaluronic acid, proteoglycan, laminin, heparin sulfate, chondroitin sulfate, keratan sulfate and matrigel, hydrogel including at least one of alginate, polyethylene glycol, silicon hydrogel, polyacrylamide, polyethylene oxide, polypyrrolidone, glycosaminoglycan and polyhema, mixture of the extracelluar matrix and the hydrogel, chemical variant of the extracelluar matrix, chemical variant of the hydrogel, or mixture of the chemical variant of the extracellular matrix and the chemical variant of the hydrogel.

The forming of the channel 75 may include preparing a substrate 10 including a first side wall WS1 connecting a lower surface LS and an upper surface US together with the lower surface LS and the upper surface US which are flat in shape to vertically face each other, a cell fixing well 20 limited to a second side wall WS2 between the lower surface LS and the upper surface US to be extended toward the lower surface LS from the upper surface US through the upper surface US in the central region of the upper surface US, and at least one passage 50 around the cell fixing well 20, and the passage 50 may be formed to be divided into a first passage 35 and a second passage 45 at both sides of the cell fixing well 20.

The substrate 10 may include transparent ceramics including glass, silicon rubbers including at least one of polydimethylsiloxane (PDMS) and ecoflex, engineering plastics including at least one of polystyrene, polymethylmethacrylate, polypropylene, polycarbonate and polyurethane, mixture including at least two of the transparent ceramics, the silicon rubbers and the engineering plastics, chemical variant of the transparent ceramics, chemical variant of the silicon rubbers, chemical variant of the engineering plastics, or mixture including at least two of the chemical variant of the transparent ceramics, the chemical variant of the silicon rubbers and the chemical variant of the engineering plastics.

The first passage 35 and the second passage 45 may be opened in the first side wall WS1 of the substrate 10 and in the second side wall WS2 of the cell fixing well 20 facing the first side wall WS1 by passing through the substrate 10.

Each of the first passage 35 and the second passage 45 may have an inlet port IP and an outlet port OP located respectively in the first side wall WS1 and the second side wall WS2.

The forming of the channel 75 may further include: inserting micro-needles 60 to the first passage 35, the cell fixing well 20, and the second passage 45; and filling the cell fixing well 20 with an ECM simulation material in a sol state.

The forming of the channel 75 may further include: curing the ECM simulation material in the sol state to transform the ECM simulation material in the sol state into the ECM simulation material 70 in the gel state; and removing the micro-needle 60 from the ECM simulation material 70 in the gel state to form the channel 75 passing through the ECM simulation material 70 in the gel state.

The forming of the brain microvessel endothelial cell lining 91 may include: injecting a brain endothelial cell 84 to the channel 75 to fix the brain endothelial cell 84 to the inner side of the channel 75; and coating the inner side of the channel 75 with the brain microvessel endothelial cell lining 91 by contacting a culture medium 88 and the brain endothelial cell 84 fixed to the inner side of the channel 75 while flowing the culture medium 88 including a brain endothelial cell into the channel 75, and the culture medium 88 may co-culture the plurality of types of human brain cells through the brain endothelial cell 84 on the inner side of the channel 75 and the ECM simulation material 70 in the gel state on the outer side of the channel 75.

The simulating of the BBB and the NVU may include: co-culturing the plurality of types of human brain cells in the ECM simulation material 70 by bringing the culture medium 88 into contact with the ECM simulation material 70 while flowing the culture medium 88 in the channel 75; and bringing the plurality of types of human brain cells into contact with the brain microvessel endothelial cell lining 91 through the channel 75.

The plurality of types of human brain cells may include one or more cells selected from the group consisting of a neuron 92, a neural stem cell 93, a microglia 94, an astrocyte 95, and a pericyte 96.

The plurality types of human brain cells may include a neuron 92, a microglia 94, an astrocyte 95, and a pericyte 96.

The BBB may include the brain microvessel endothelial cell lining 91, the astrocyte 95, and the pericyte 96.

The NVU may include the BBB, the neuron 92, the neural stem cell 93, and the microglia 94.

The 3D co-culture in which the NVU of the human brain is simulated may be performed by bringing the outer side of the channel 75 into contact with the ECM simulation material 70 in the gel state, and a tested drug may be negligibly absorbed on the substrate 10 by minimizing the contact between the substrate 10 and the channel 75 to avoid showing a different aspect from a mechanism in vivo.

A neurovascular unit (NVU)-on-a-chip according to the exemplary embodiment of the present disclosure, in that a cell fixing well and passages at both sides of the cell fixing well, which are all positioned in a substrate, are used in order of the passages to face each other through an inside of the cell fixing well, and also an extracelluar matrix (ECM) simulation material is mounted in the cell fixing well to communicate the passages of the substrate with channels of the ECM simulation material one-to-one, can be configured to 3-dimensionally co-culture a brain microvessel endothelial cell lining sufficiently covering an inner side of each of the channels, and a plurality of types of human brain cells which is positioned along the brain microvessel endothelial cell lining on an outer side of the each of the channels in the ECM simulation material, during a repeated flow of a culture medium in the passages and the channels.

Further, the neurovascular unit (NVU)-on-a-chip, in that the brain microvessel endothelial cell lining surrounding the inner side of the channel and the plurality of types of human brain cells in the ECM simulation material defining the channel are 3-dimensionally co-cultured to bring the plurality of types of human brain cells into directly contact with the brain microvessel endothelial cell lining, can easily simulate a brain blood barrier (BBB) of the human brain and the neurovascular unit (NVU) of the human brain including the BBB and minimize the contact between the substrate and the channel in order that a tested drug is negligibly absorbed on the substrate to avoid showing a different aspect from a mechanism in vivo.

Furthermore, the neurovascular unit (NVU)-on-a-chip can make a new market for brain-disease and bio fields, in that an incurable brain disease validation estimation platform, which simulates the BBB of the human brain and the NVU of the human brain including the BBB on the substrate, enables a personalized brain disease treatment technology to develop within a short time and also an developed technology of the incurable brain disease validation estimation platform is able to be extended and applied to other human diseases.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a perspective view schematically showing a neurovascular unit (NVU)-on-a-chip according to an exemplary embodiment of the present disclosure.

FIG. 2 is a cross-sectional view schematically showing an extra-cellular matrix simulation material taken in a region A of FIG. 1.

FIG. 3 shows a schematic diagram illustrating a method of fabricating the NVU-on-a-chip of FIG. 1.

FIG. 4 shows a schematic diagram illustrating a method of fabricating the NVU-on-a-chip of FIG. 1.

FIG. 5 shows a schematic diagram illustrating a method of fabricating the NVU-on-a-chip of FIG. 1.

FIG. 6 shows a schematic diagram illustrating a method of fabricating the NVU-on-a-chip of FIG. 1.

FIG. 7 shows a schematic diagram illustrating a method of fabricating the NVU-on-a-chip of FIG. 1.

FIG. 8 shows a schematic diagram illustrating a method of fabricating the NVU-on-a-chip of FIG. 1.

FIG. 9 shows a schematic diagram illustrating a method of fabricating the NVU-on-a-chip of FIG. 1.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure will be described with reference to the accompanying drawings based on a specific embodiment in which the present disclosure may be carried out as an example. The embodiment will be sufficiently described in detail enough to carry out the present disclosure by those skilled in the art. It should be understood that various embodiments of the present disclosure are different from each other, but need not to be mutually exclusive. For example, a specific figure, a structure, and a characteristic described herein may be implemented as another embodiment without departing from a spirit and a scope of the present disclosure in relation to an embodiment. Further, it should be understood that a position or a displacement of an individual constituent element in each disclosed embodiment may be changed without departing from the spirit and the scope of the present disclosure. Accordingly, a detailed description below is not taken as a limited meaning, and is defined by the accompanying claims together with all equivalent scopes to the claims if the scope of the present disclosure is appropriately described. In the drawings, like reference numerals designate like or similar functions over various aspects and lengths, areas, thicknesses, and the like and shapes thereof can be exaggeratedly expressed for convenience.

Hereinafter, the exemplary embodiments of the present disclosure will be described with reference to the accompanying drawings in detail so that those skilled in the art may easily carry out the present disclosure.

FIG. 1 is a perspective view schematically showing a neurovascular unit (NVU)-on-a-chip according to an exemplary embodiment of the present disclosure and FIG. 2 is a cross-sectional view schematically showing an extra-cellular matrix simulation material taken in a region A of FIG. 1.

Referring to FIGS. 1 and 2, a neurovascular unit (NVU)-on-a-chip 100 according to the present disclosure includes a substrate 10, an extracellular matrix (ECM) simulation material 70, and a plurality of channels 75. The substrate 10 is configured to mount the ECM simulation material 70 in a cell fixing well 20 which is positioned between a lower surface LS and an upper surface US so as to be extended toward the lower surface LS from the upper surface US passing through the upper surface US in a central region of the substrate 10.

The substrate 10 may include transparent ceramics including glass, silicon rubbers including at least one of polydimethylsiloxane (PDMS) and ecoflex, engineering plastics including at least one of polystyrene, polymethylmethacrylate, polypropylene, polycarbonate and polyurethane, mixture including at least two of the transparent ceramics, the silicon rubbers and the engineering plastics, chemical variant of the transparent ceramics, chemical variant of the silicon rubbers, chemical variant of the engineering plastics, or mixture including at least two of the chemical variants of the transparent ceramics, the chemical variants of the silicon rubbers and the chemical variants of the engineering plastics.

The substrate 10 and the cell fixing well 20 is quadrangular in shape and have a first side wall WS1 and a second side wall WS2, respectively. The first side wall WS1 has a larger height than the second side wall WS2 in a thickness direction of the substrate 10. The first side wall WS1 and the second side wall WS2 come into contact with the upper surface US while forming an angle with the upper surface US to face each other. The ECM simulation material 70 is in a gel state and contains a plurality of types of human brain cells as illustrated in FIG. 2. Preferably, the plurality of types of human brain cells includes a neuron 92, a microglia 94, an astrocyte 95, and a pericyte 96.

As an example, the plurality of types of human brain cells may include one or more cells selected from the group consisting of the neuron 92, a neural stem cell 93, the microglia 94, the astrocyte 95, and the pericyte 96. In case of using the NVU-on-a-chip 100 according to the present disclosure, the NVU-on-a-chip 100 may simultaneously co-culture five types of brain cells described above.

Cell used for analyzing the efficacy and the stability as to development of agents for treating brain diseases use mostly a single type of brain cell cultured in vitro. Even in case of using two to three types of cells together, the 2-dimensionally cultured brain cells were often targeted. Recently, a technique of 3-dimensionally culturing the single type of cell or the two to three types of cells in a spheroid shape has been developed and used.

Meanwhile, the NVU-on-a-chip 100 is configured to culture one or more cells selected from the group consisting of a brain microvessel endothelial cell lining 91, the neuron 92, the neural stem cell 93, the microglia 94, the astrocyte 95 and the pericyte 96 in a 3-dimensional form, and the brain microvessel endothelial cell lining 91, the neuron 92, the neural stem cell 93, the microglia 94, the astrocyte 95 and the pericyte 96 may be obtained and used from the human brain tissue.

As one type of cell existing in the brain tissue constituting the human brain, the neuron 92 refers to a nerve cell as a unit forming a nervous system. The neural stem cell 93 is a cell capable of self-reproduction and having differentiation potency to a nerve cell. Further, the microglia 94 is referred to as a neuroglial cell or a microglial cell of the central nervous system derived from the mesoderm, and acts as a phagocyte which takes charge of carrying, breaking, and removing materials in the brain tissue. In addition, the microglia 94 not only serves to support the tissue of the central nervous system, but also functions to supply a material required for the nerve cell and create a chemical environment suitable for activity of the nerve cell.

Further, the astrocyte 95 is also called an astroglia cell as one of cells consisting a neuroglia which supports the nervous tissue, is a small cell body and has projections branched in many directions, and serves to help a structure and a mechanism of the neuron. In view of an occupation region of the pericyte 96 on a capillary wall, the capillary wall is composed of only the flat endothelial cells and clearly has no a smooth muscle layer or a connective tissue layer surrounding a periphery of the endothelial cell, wherein a connective tissue cell is appeared scatteredly on the basement membrane of the endothelial cell, and it is well known that the connective tissue cell has phagocytosis as the pericyte 96.

The brain cells 92, 93, 94, 95, and 96 described above are 3-dimensionally present in the brain as cells present in the brain tissue, and it could be seen that the NVU-on-a-chip 100 may successfully co-culture the brain cells 92, 93, 94, 95, and 96 in vitro so as to simulate the brain tissue in vivo including a blood-brain barrier.

Here, cell culture is a very important process in cell biology, tissue engineering, biomedical engineering, pharmacokinetic for drug development and the like, and the in-vitro cell culture enables various cells to be plentifully cultured. However, the vitro cultured cells are not equal to cell grown in vivo and the reason is that biological system environments in vivo and in vitro are different from each other.

Further, the co-culture in which different cells derived from the same tissue or the same organ are cultured together has need to maintain specific activity of the cells as it is while cells to be cultured survive well, but when the different cells are cultured together, it is not easy to establish the foregoing condition.

However, the present disclosure helps to make a condition capable of co-culturing various types of brain cells together to be similar to the 3D brain tissue including the blood-brain barrier which has various types of brain tissue cells. Further, the ECM simulation material 70 according to the present disclosure is a material capable of equally or similarly implementing the ECM in the human brain and is not limited thereto. However, the ECM simulation material 70 may include an extracelluar matrix including at least one of collagen, fibronectin, fibrin, fibrinogen, elastin, hyaluronic acid, proteoglycan, laminin, heparin sulfate, chondroitin sulfate, keratan sulfate and matrigel, hydrogel including at least one of alginate, polyethylene glycol, silicon hydrogel, polyacrylamide, polyethylene oxide, polypyrrolidone, glycosaminoglycan and polyhema, mixture of the extracelluar matrix and the hydrogel, chemical variant of the extracelluar matrix, chemical variant of the hydrogel, or mixture of the chemical variant of the extracelluar matrix and the chemical variant of the hydrogel.

The plurality of channels 75 is formed through the ECM simulation material 70. The ECM simulation material 70 may limit one channel 75. The plurality of channels 75 is positioned in parallel in the ECM simulation material 70, but is not limited thereto. The plurality of channels 75 may perfuse a culture medium 88 of FIG. 9. A brain microvessel endothelial cell lining 91 is formed on an inner side of each channel 75. Herein, the ECM simulation material 70 contains a plurality of types of human brain cells on the outer side of the channel 75 or around the channel 75. In this case, the brain microvessel endothelial cell lining 91 forms a blood brain barrier (BBB) together with the astrocyte 95 and the pericyte 96 which are co-cultured in the ECM simulation material 70.

The brain microvessel endothelial cell lining 91 is closely positioned along the inner side of the channel 75 to coat or sufficiently cover the inner side of the channel 75. Meanwhile, the substrate 10 includes a passage 50 having the same number as the channel 75. The passage 50 is divided into a first passage 35 and a second passage 45 at both sides of the cell fixing well 20 to pass through the substrate 10 and fluidly communicate with the channel 75.

The first passage 35 and the second passage 45 are opened in the first side wall WS1. As described above, the NVU-on-a-chip 100 includes the substrate 10, the ECM simulation material 70 and the plurality of channels 75 to simulate a structure of the BBB of the human brain and a structure of the NVU including the BBB in the human brain by bringing the plurality of types of human brain cells into contact with the brain microvessel endothelial cell lining 91 through the plurality of channels 75.

The NVU is implemented on the basis of the BBB, the neuron 92, the neural stem cell 93, and the microglia 94. Further, the outer side of the channel 75 comes into contact with the ECM simulation material 70 and thus the NVU-on-a-chip 100 enables a 3D co-culture so as to simulate the NVU of the human brain including the BBB.

Further, a tested drug (not illustrated) can be negligibly absorbed on the substrate 10 due to minimizing the contact of the substrate 10 and the channel 75 to avoid showing a different aspect from a mechanism in vivo.

FIGS. 3 to 9 are schematic diagrams illustrating a method of fabricating the NVU-on-a-chip of FIG. 1.

Referring to FIGS. 3 to 9, a method of fabricating the NVU-on-a-chip according to the present disclosure may include forming a channel 75 (see FIG. 7) passing through an ECM simulation material 70 (see FIG. 7) containing the plurality of types of human brain cells in a gel state. In this case, the ECM simulation material 70 may include an extracelluar matrix including at least one of collagen, fibronectin, fibrin, fibrinogen, elastin, hyaluronic acid, proteoglycan, laminin, heparin sulfate, chondroitin sulfate, keratan sulfate and matrigel, hydrogel including at least one of alginate, polyethylene glycol, silicon hydrogel, polyacrylamide, polyethylene oxide, polypyrrolidone, glycosaminoglycan and polyhema, mixture of the extracelluar matrix and the hydrogel, chemical variant of the extracelluar matrix, chemical variant of the hydrogel, or mixture of the chemical variant of the extracelluar matrix and the chemical variant of the hydrogel.

The forming of the channel 75 may first include preparing a substrate including a first side wall WS1 connecting a lower surface LS and an upper surface US together with the lower surface LS and the upper surface US which are flat in shape to vertically face each other, a cell fixing well 20 limited to a second side wall WS2 between the lower surface LS and the upper surface US so as to be extended toward the lower surface LS from the upper surface US through the upper surface US in the central region of the upper surface US, and at least one passage 50 around the cell fixing well 20.

The substrate 10 may include transparent ceramics including glass, silicon rubbers including at least one of polydimethylsiloxane (PDMS) and ecoflex, engineering plastics including at least one of polystyrene, polymethylmethacrylate, polypropylene, polycarbonate and polyurethane, mixture including at least two of the transparent ceramics, the silicon rubbers and the engineering plastics, chemical variant of the transparent ceramics, chemical variant of the silicon rubbers, chemical variant of the engineering plastics, or mixture including at least two of the chemical variants of the transparent ceramics, the chemical variants of the silicon rubbers and the chemical variants of the engineering plastics.

The passage 50 may be formed to be divided into a first passage 35 and a second passage 45 at both sides of the cell fixing well 20. The first passage 35 and the second passage 45 are opened in the first side wall WS1 of the substrate 10 and in the second side wall WS2 of the cell fixing well 20 facing the first side wall WS1 by passing through the substrate 10. The first passage 35 and the second passage 45 are formed in the substrate 10 to face each other along a straight line in the cell fixing well 20.

Each of the first passage 35 and the second passage 45 may have an inlet port IP and an outlet port OP located respectively in the first side wall WS1 and the second side wall WS2. The forming of the channel 75 may further include inserting a micro-needle 60 to the first passage 35, the cell fixing well 20, and the second passage 45 and filling the cell fixing well 20 with an ECM simulation material (not shown) in a sol state. In this case, the micro-needle 60 may pass through the first passage 35 in a first direction D1 to be inserted in the second passage 45 via the cell fixing well 20.

The ECM simulation material in the sol state is formed along the micro-needle 60 in the cell fixing well 20 to cover the micro-needle 60 by contacting the micro-needle 60 and surrounding the micro-needle 60. In this case, the plurality of types of human brain cells are contained in the ECM simulation material which is in the sol state, and preferably, may include a neuron, a microglia, an astrocyte and a pericyte.

As an example, the plurality of types of human brain cells may also include one or more cells selected from the group consisting of the neuron, a neural stem cell, the microglia, the astrocyte, and the pericyte. Further, the forming of the channel 75 may further include curing the ECM simulation material in the sol state to transform the ECM simulation material in the sol state into the ECM simulation material 70 in the gel state, and removing the micro-needle 60 from the ECM simulation material 70 in the gel state to form the channel 75 passing through the ECM simulation material 70 in the gel state.

The ECM simulation material 70 in the gel state may be formed by applying heat at a predetermined temperature to the ECM simulation material in the sol state. The micro-needle 60 may go through the second passage 45 of the substrate 10 in a second direction D2 to be separated from the first passage 35 of the substrate 10 via the channel 75 of the ECM simulation material 70. After the forming of the channel 75 is completed, forming a brain microvessel endothelial cell lining 91 on an inner side of the channel 75 may be performed.

The forming of the brain microvessel endothelial cell lining 91 may include injecting a brain endothelial cell 84 into the channel 75 to fix the brain endothelial cell 84 to the inner side of the channel 75; and coating the inner side of the channel 75 with the brain microvessel endothelial cell lining 91 by contacting a culture medium 88 and the brain endothelial cell 84 fixed to the inner side of the channel 75 while flowing the culture medium 88 including a brain endothelial cell into the channel 75. The culture medium 88 may co-culture the plurality of types of human brain cells through the brain endothelial cell on the inner side of the channel 75 and the ECM simulation material 70 in the gel state in the outer side of the channel 75.

The fixing of the brain endothelial cell 84 may be performed by flowing a brain endothelial cell injection into the first passage 35 of the substrate 10, the channel 75 of the ECM simulation material 70 and the second passage 45 of the substrate 10 along a first flow line F1, and then sparsely attaching the brain endothelial cell 84 to the inner side of the channel 75 of the ECM simulation material 70 during the flow of the brain endothelial cell injection as shown in FIG. 8.

In this case, the culture medium 88 may be repetitively flowed to the first passage 35 of the substrate 10, the channel 75 of the ECM simulation material 70 and the second passage 45 of the substrate 10, and then the second passage 45 of the substrate 10, the channel 75 of the ECM simulation material 70 and the first passage 35 of the substrate 10 along a second flow line F2. The culture medium 88 may form the brain microvessel endothelial cell lining 91 on the inner side of the channel 75 as shown in FIG. 1 by proliferating, culturing or growing the brain endothelial cell 84 of FIG. 8 which is sparsely attached on the inner side of the channel 75 while flowing into the substrate 10 and the ECM simulation material 70 along the second flow line F2 as shown in FIG. 9.

The brain microvessel endothelial cell lining 91 is formed along the inner side of the channel 75 to cover the inner side of the channel 75. After the brain microvessel endothelial cell lining 91 is formed, simulating a BBB of the human brain and an NVU of the human brain including the BBB through the channel 75 by using the brain microvessel endothelial cell lining 91 and the plurality of types of human brain cells is performed. Herein, the simulating of the BBB and the NVU may include co-culturing the plurality of types of human brain cells in the ECM simulation material 70 by bringing the culture medium 88 into contact with the ECM simulation material 70 during the flow of the culture medium 88 in the channel 75; and bringing the plurality of types of human brain cells into contact with the brain microvessel endothelial cell lining 91 through the channel 75.

In this case, the plurality of types of human brain cells may include the neurons 92, the neural stem cells 93, the microglia 94, the astrocytes 95 and the pericytes 96 which come into contact with the brain microvessel endothelial cell lining 91, as shown in FIG. 2. The BBB may include the brain microvessel endothelial cell lining 91, the astrocyte 95, and the pericyte 96. The NVU may include the BBB, the neuron 92, the neural stem cell 93, and the microglia 94.

As a result, the substrate 10 and the ECM simulation material 70 may configure the NVU-on-a-chip 100 (see FIG. 1) by using the structure of the NVU implemented in the ECM simulation material 70. Herein, the 3D co-culture in which the NVU of the human brain including the BBB is simulated may be performed by bringing the outer side of the channel 75 into contact with the ECM simulation material 70, and a tested drug is negligibly absorbed on the substrate 10 by minimizing the contact between the substrate 10 and the channel 75 to avoid showing a different aspect from a mechanism in vivo.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of fabricating a neurovascular unit (NVU)-on-a-chip, comprising:
   forming a channel on a chip, passing through an extracellular matrix (ECM) simulation material containing a plurality of types of human-derived brain cells in a gel state;
   forming a human brain microvessel endothelial cell lining on an intraluminal surface of the channel;
   stabilizing the brain microvessel endothelial cell lining formed on the intraluminal surface by circulating a culture medium for co-culture in the channel thereby simulating and maintaining a blood brain barrier (BBB) of a human brain constituted by a plurality of human-derived brain tissue cells which are 3-dimensionally positioned around the channel on the chip of the neurovascular unit (NVU), wherein a plurality of types of human-derived brain cells consists of neuron, microglia, astrocyte, pericyte and neuron stem cell.

2. The method of fabricating the NVU-on-a-chip of claim 1, wherein the ECM simulation material comprises
an extracelluar matrix,
a hydrogel, or
a mixture of the extracellular matrix and the hydrogel.

3. The method of fabricating the NVU-on-a-chip of claim 1, further comprising preparing a substrate in which the extracellular matrix is placed, wherein the substrate comprises a first side wall (WS1) connecting a lower surface (LS) and an upper surface (US) together with the lower surface (LS) and the upper surface (US) which are flat in shape to vertically face each other, a cell fixing well limited to a second side wall (WS2) between the lower surface (LS) and the upper surface (US) to be extended toward the lower surface (LS) from the upper surface (US) through the upper surface (US) in the central region of the upper surface (US), and at least one passage around the cell fixing well, and the passage is formed to be divided into a first passage and a second passage at both sides of the cell fixing well.

4. The method of fabricating the NVU-on-a-chip of claim 3, wherein the substrate comprises
transparent ceramics comprising glass,
silicon rubbers comprising polydimethylsiloxane (PDMS) or ecoflex,
engineering plastics comprising polystyrene, polymethylmethacrylate, polypropylene, polycarbonate or polyurethane, or
a mixture comprising at least two of the transparent ceramics, the silicon rubbers and the engineering plastics.

5. The method of claim 4, wherein
the transparent ceramics comprises glass,
the silicon rubbers comprises polydimethylsiloxane (PDMS) or ecoflex, and
the engineering plastics comprises polystyrene, polymethylmethacrylate, polypropylene, polycarbonate or polyurethane.

6. The method of fabricating the NVU-on-a-chip of claim 3, wherein the first passage and the second passage are open in the first side wall (WS1) of the substrate and in the second side wall (WS2) of the cell fixing well facing the first side wall (WS1) by passing through the substrate.

7. The method of fabricating the NVU-on-a-chip of claim 3, wherein each of the first passage and the second passage has an inlet port (IP) and an outlet port (OP) located respectively in the first side wall (WS1) and the second side wall (WS2).

8. The method of fabricating the NVU-on-a-chip of claim 3, wherein the forming of the channel further includes: inserting a micro-needle to the first passage, the cell fixing well, and the second passage; and filling the cell fixing well with an ECM simulation material in a sol state.

9. The method of fabricating the NVU-on-a-chip of claim 8, wherein the forming of the channel further includes: curing the ECM simulation material in the sol state to transform the ECM simulation material in the sol state into the ECM simulation material in the gel state; and removing the micro-needle from the ECM simulation material in the gel state to form the channel passing through the ECM simulation material in the gel state.

10. The method of fabricating the NVU-on-a-chip of claim 1, wherein the forming of the human brain microvessel endothelial cell lining comprises:
fixing a brain endothelial cell to the intraluminal surface of the channel by injecting the brain endothelial cell to the channel; and
stabilizing the brain microvessel endothelial cell lining fixed to the intraluminal surface of the channel comprising contacting culture medium with the brain endothelial cell fixed to the intraluminal surface of the channel while perfusing the culture medium in the channel,
wherein the culture medium allows for co-culturing the brain endothelial cell fixed and stabilized to the intraluminal surface of the channel and the plurality of types of human-derived brain cells positioned in the ECM simulation material in the gel state, which are 3-dimensionally positioned around the channel.

11. The method of fabricating the NVU-on-a-chip of claim 10, wherein the simulating of the BBB on the NVU comprises:
culturing the plurality of types of human-derived brain cells in the ECM simulation material by diffusing the culture medium to the ECM simulation material while flowing the culture medium circulated and perfused in the channel; and
contacting 3-dimensionally the plurality of types of human-derived brain cells and the brain microvessel endothelial cell lining based on the channel.

12. The method of fabricating the NVU-on-a-chip of claim 11, wherein the plurality of types of human brain cells include one or more cells selected from the group consisting of a neuron, a neural stem cell, a microglia, an astrocyte, and a pericyte.

13. The method of fabricating the NVU-on-a-chip of claim 12, wherein the BBB includes the brain microvessel endothelial cell lining, the astrocyte, and the pericyte.

14. The method of fabricating the NVU-on-a-chip of claim 13, wherein the NVU includes the BBB, the neuron, the neural stem cell, and the microglia.

15. The method of fabricating the NVU-on-a-chip of claim 11, wherein the plurality of types of human brain cells include a neuron, a microglia, an astrocyte, and a pericyte.

* * * * *